US012758954B2

(12) United States Patent
Rodriguez et al.

(10) Patent No.: US 12,758,954 B2
(45) Date of Patent: Oct. 13, 2026

(54) CATALYST SYSTEM AND PROCESS FOR PRODUCING BISPHENOL-A

(71) Applicant: BADGER LICENSING LLC, Boston, MA (US)

(72) Inventors: Mariam Salazar Rodriguez, Braintree, MA (US); Chung-Ming Chi, Needham, MA (US)

(73) Assignee: BADGER LICENSING LLC, Boston, MA (US)

(*) Notice: Subject to any disclaimer, the term of this patent is extended or adjusted under 35 U.S.C. 154(b) by 601 days.

(21) Appl. No.: 18/036,401

(22) PCT Filed: Nov. 12, 2020

(86) PCT No.: PCT/US2020/060177
§ 371 (c)(1),
(2) Date: May 10, 2023

(87) PCT Pub. No.: WO2022/103394
PCT Pub. Date: May 19, 2022

(65) Prior Publication Data
US 2024/0001352 A1 Jan. 4, 2024

(51) Int. Cl.
*B01J 31/02* (2006.01)
*B01J 21/08* (2006.01)
(Continued)

(52) U.S. Cl.
CPC ........... *B01J 31/0225* (2013.01); *B01J 21/08* (2013.01); *B01J 31/0217* (2013.01); *B01J 35/80* (2024.01);
(Continued)

(58) Field of Classification Search
CPC ........ B01J 21/08; B01J 27/02; B01J 31/0217; B01J 31/0225; B01J 35/80; B01J 37/0209;
(Continued)

(56) References Cited

U.S. PATENT DOCUMENTS 5,169,992 A 12/1992 Knifton et al.
5,631,338 A 5/1997 Inoue et al.
(Continued)

FOREIGN PATENT DOCUMENTS

CN 201810635572 A 12/2018
EP 0771589 A1 5/1997
(Continued)

OTHER PUBLICATIONS

Oliveira de Magalhães, G. et al., 2018, Materials Research, 21(6), 6 pp. <http://dx.doi.org/10.1590/1980-5373-MR-2018-0148> (Year: 2018).*

(Continued)

*Primary Examiner* — Brian A Mccaig
(74) *Attorney, Agent, or Firm* — Kilpatrick Townsend & Stockton LLP

(57) ABSTRACT

Described is a catalyst system useful in the production of bisphenol-A comprises (a) an acidic heterogeneous catalyst comprising amorphous silica having organosulfonic acid groups chemically bonded thereto, wherein the catalyst has a pKa value of 3.5 or less; and (b) a catalyst promoter comprising at least one organic sulfur-containing compound.

10 Claims, 5 Drawing Sheets

(51) Int. Cl.
*B01J 35/80* (2024.01)
*C07C 37/20* (2006.01)

(52) U.S. Cl.
CPC ....... *C07C 37/20* (2013.01); *B01J 2231/4288* (2013.01); *B01J 2531/007* (2013.01)

(58) Field of Classification Search
CPC ......... B01J 2231/4288; B01J 2531/007; C07C 37/20
See application file for complete search history.

(56) References Cited

U.S. PATENT DOCUMENTS

| | | | |
|---|---|---|---|
| 5,919,566 A | 7/1999 | Lansink-Rotgerink et al. | |
| 6,051,658 A | 4/2000 | Wehmeyer | |
| 6,229,037 B1 | 5/2001 | Okubo et al. | |
| 7,815,883 B2 | 10/2010 | Cheng et al. | |
| 2010/0069677 A1* | 3/2010 | Hoshino | C07C 29/50 568/376 |
| 2020/0047170 A1 | 2/2020 | Papile | |

FOREIGN PATENT DOCUMENTS

| | | |
|---|---|---|
| JP | 09173885 A | 7/1997 |
| WO | 2013061274 A1 | 5/2013 |

OTHER PUBLICATIONS

International Search report and Written Opinion issued in the corresponding Application No. PCT/US2020/060177 on Jul. 21, 2021.

Chen et al, "Dual-functionalized large pore mesoporous silica as an efficient catalyst for bisphenol-A synthesis", Microporous and Mesoporous Materials, Elsevier, Amsterdam ,NL, vol. 109, No. 1-3, Dec. 21, 2007 (Dec. 21, 2007), p. 258-270.

Margelefsky E., Bendjeriou, Zeidan R., Dufaud V., Davis M. Nanoscale Organization of thiol and arulsulfonic acid on silica leads a highly active and selective bifunctional, heterogeneous catalyst. J. Am. Che. Soc. 130 (2008) 13442.

Davis M., Dufaud V. Design of heterogeneous catalysts via multiple active site positioning in organic-inorganic hybrid materials. J. Am. Che. Soc. 125 (2003) 9403.

Zeidan R., Dufaud V., Davis M. Enhanced cooperative, catalytic behavior of organic functional groups by Immobilization. J. of Catalysis. 239 (2006) 299.

http://www.silicycle.com/.

http://www.norpro.saint-gobain.com/sites/imdf.norpro.com/files/sgnorpro-standard-catalyst-carriers-list-2016_0.pdf.

SILSOL® Silica Active Ingredient Technology, Available online at: https://grace com./products/silsol/.one copy. end., Accessed from Internet on Dec. 4, 2025, pp. 1-2.

Das et al., Selective Synthesis of Bisphenol-A Over Mesoporous MCM Silica Catalysts Functionalized with Sulfonic Acid Groups, Journal of Catalysis, vol. 223, No. 1, Apr. 2004, pp. 152-160.

Korean Application No. 10-2023-7019653, Office Action mailed on Dec. 8, 2025, 20 pages (9 pages of original document and 11 pages of English Translation).

International Application No. PCT/US2020/060177, International Preliminary Report on Patentability mailed on May 25, 2023, 8 pages.

Singaporean Application No. 11202303579V, Written Opinion mailed on Oct. 30, 2025, 9 pages.

* cited by examiner

CATALYST SYSTEM AND PROCESS FOR PRODUCING BISPHENOL-A

CROSS-REFERENCE TO RELATED APPLICATIONS

The present application is a U.S. National Phase of PCT/US2020/060177 filed on Nov. 12, 2020. The disclosure of the PCT Application is hereby incorporated by reference into the present Application.

FIELD

This invention relates to a catalyst system and process for producing bisphenol-A.

BACKGROUND

Bisphenol-A (BPA), also referred to as 2,2-bis (4-hydroxyphenyl) propane or para, para-diphenylolpropane (p,p-BPA), is a commercially important precursor used in the manufacture of polycarbonates, other engineering thermoplastics and epoxy resins. The polycarbonate application in particular demands high purity BPA due to stringent requirements for optical clarity and color in the finished application.

BPA is produced commercially by the condensation of acetone and phenol and, in fact, BPA production is the largest consumer of phenol. The reaction may take place in the presence of a strong homogenous acid, such as hydrochloric acid, sulfuric acid, or toluene sulfonic acid, or in the presence of a heterogeneous acid catalyst, such as a sulfonated ion exchange resin. In recent years, acidic ion exchange resins (IERs) have become the overwhelming choice as catalysts for the condensation reaction in bisphenol manufacture. Particularly useful IERs are sulfonated polystyrene ion exchange resins, in which sulfonic acid groups are chemically bonded to a backbone polystyrene resin. In some cases, an organic mercapto group, such as a mercaptoalkylamine, is also chemically bonded to the backbone polystyrene resin as a cocatalyst (see, for example, U.S. Pat. No. 6,051,658). In other cases, an organic mercaptan, such as methyl or ethyl mercaptan, or a mercaptocarboxylic acid, such as 3-mercaptopropionic acid, is freely circulated in the BPA reaction mixture separately from the IER catalyst.

Despite their wide application in bisphenol manufacture, IER-based catalysts suffer from a number of disadvantages. For example, IERs operate over a limited range of temperatures to prevent desulfonation or catalyst degradation. It also is well known that cation exchange resins swell and shrink depending on the chemical environment. The BPA process is designed to be adapted to the resin volume changes and its poor mechanical resistance, thus up-flow bed reactors are commonly used. The low structural integrity of IER is the result of a low degree of crosslinking or a low content of divinylbenzene in the styrene-divinylbenzene copolymer which is needed to control IER pore size, accessibility to the active sites and activity. Low crosslinking levels of IER lead to increased compressibility values, which can contribute to an increased pressure drop though the catalyst bed in the reactor, and which ultimately limits the BPA production. IER not only exhibits a low structural integrity but also low chemical integrity due to sulfonic acid group leach. The excess of acid is removed during BPA reactor start-ups and acid concentration is monitored during operation, as the presence of leached acid negatively impacts BPA product purity.

There is therefore significant interest in developing improved catalyst systems and processes for the production of bisphenol-A.

SUMMARY

According to the present invention, it has now been found that functionalized silica catalysts, in which organosulfonic acid groups are bonded to a silica backbone, offer a higher conversion rate and higher selectivity to p,p-BPA over IER catalysts. An additional advantage of the functionalized silica over polymer-based materials is their rigid structure, which prevents thermal or chemical degradation. Functionalized silica catalysts exhibit a defined pore structure and constant volume independent of the chemical environment, temperature and pressure. This pore structure can be manipulated during the catalyst preparation to control properties such as surface area, pore size and volume, form and size of particles, and chemical surface.

Thus, in one aspect, the present invention resides in a catalyst system useful in the production of bisphenol-A comprising:

(a) an acidic heterogeneous catalyst comprising amorphous silica having organosulfonic acid groups chemically bonded thereto, wherein the catalyst has a pKa value of 3.5 or less; and (b) a catalyst promoter comprising at least one organic sulfur-containing compound.

In a further aspect, the present invention resides in a process for producing bisphenol-A by the reaction of acetone and phenol in a reaction medium in the presence of a catalyst system, wherein the catalyst system comprises:

a) an acidic heterogeneous catalyst comprising amorphous silica having organosulfonic acid groups chemically bonded thereto, wherein the catalyst has a pKa value of 3.5 or less; and (b) a catalyst promoter comprising at least one organic sulfur-containing compound.

DETAILED DESCRIPTION OF THE EMBODIMENTS

Figure 1:
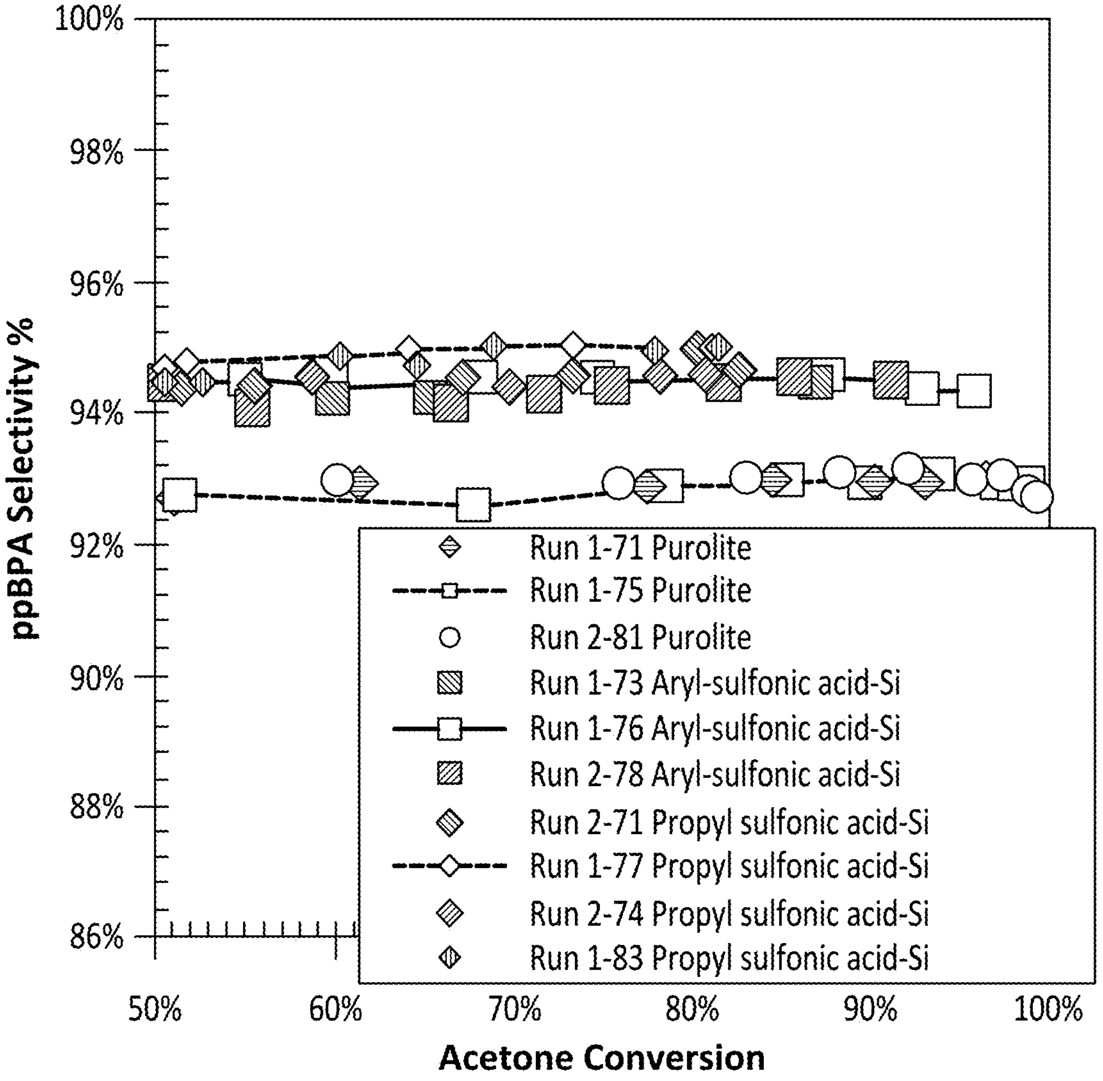
FIG. 1 is a graph of p,p-BPA selectivity against acetone conversion for a commercial ion exchange resin (Purolite® CT-122), an alkylsulfonic acid silica and an arylsulfonic acid silica in the condensation of phenol and acetone according to the process of Example 1.

Described herein is a catalyst system comprising (a) an acidic heterogeneous catalyst comprising amorphous silica having organosulfonic acid groups chemically bonded thereto, wherein the catalyst has a pKa value of 3.5 or less; and (b) a catalyst promoter comprising at least one organic sulfur-containing compound. Also described herein are uses of the catalyst system in condensation reactions, such as the condensation of carbonyl compounds with phenolic compounds to produce polyphenols and especially the condensation of phenol with acetone to produce bisphenol-A (BPA).

The pKa values referred to herein are measured by titration using a dispersion 0.15 g of the catalyst in 40 gr of a NaCl/water solution (2.5% wt). The resulting slurry is left for a minimum of 4 hours under agitation. Then the titration is performed using a solution of NaOH (0.1-0.01 N). The pKa is determined at half titration point in the titration curve. At this point the concentrations of base and acid are equal, and therefore the pKa is equivalent to the pH. At least three titrations are carried out for each material and the average of the three pKa values is reported in terms of meq/g.

Acidic Heterogeneous Catalyst

The acidic heterogeneous catalyst employed in the present catalyst system comprises amorphous silica functionalized with organosulfonic acid groups, such that the catalyst has a pKa value of 3.5 or less. The amorphous silica conveniently comprises silica particles, either in the form of a free-running powder (that is, in which the silica particles are physically separate) or in the form of shaped objects, such as extrudates, in which the silica particles are composited together with or without the aid of a binder. In embodiments, the amorphous silica is substantially free of zirconium, such that, for example, the amorphous silica contains less than 1 wt. %, such as less than 0.5 wt. %, such as less than 0.05 wt. % and preferably no measurable amount of zirconium.

As used herein the term "amorphous" is used in its commonly accepted sense to mean lacking long range order such as would give rise to one or more intense peaks in an X-ray diffraction pattern.

The amorphous silica may be functionalized with one or more organosulfonic acid groups having the following formula $-R^1SO_3H$ where $R^1$ is chemically bonded to the silica and comprises a substituted or unsubstituted alkyl, alkenyl, alkynyl group, preferably having up to 8 carbon atoms, or is a substituted or unsubstituted aryl group. In embodiments, $R^1$ is an alkyl group, such as an alkyl group having from 1 to 4 carbon atoms, such functionalized silicas also being referred to herein as alkylsulfonic acid silicas. In other embodiments, $R^1$ is an aryl group, such as an alkyl-substituted phenyl group in which the alkyl moiety has from 1 to 4 carbon atoms, such functionalized silicas also being referred to herein as arylsulfonic acid silicas. Non-limiting examples of suitable organosulfonic acid functionalized silica compounds having the required pKa value of 3.5 or less include methanesulfonic acid silica, ethanesulfonic acid silica, propanesulfonic acid silica, butanesulfonic acid silica, benzenesulfonic acid silica, ethylbenzenesulfonic acid silica, vinylbenzenesulfonic acid silica, propylbenzenesulfonic acid silica, butylbenzene sulfonic acid silica.

A number of organosulfonic acid functionalized silica compounds having a pKa value of 3.5 or less are commercially available. In addition, synthesis methods for production of organosulfonic acid functionalized silica compounds having a pKa value of 3.5 or less are well known. Exemplary methods include (a) postfunctionalization of an existing silica support by reaction of silanol groups on the support with an alkoxysilane containing a thiol group, such as 3-mercaptopropyltrimethoxysilane (MPTMS) and 2) co-condensation of an alkoxysilane containing a thiol group, such as MPTMS, with a silicon source, usually siloxane precursors (e.g., tetraethyl orthosilicate, TEOS, or tetramethyl orthosilicate, TMOS). The final step in the production of the functionalized silica is the oxidation of the thiol groups to sulfonic acids by using oxidants, such as $H_2O_2$.

Organic Sulfur Promoter

The present catalyst system also includes at least one organic sulfur-containing promoter, which generally contains at least one thiol, S—H, group. Such thiol promoters can be either ionically or covalently bonded to the heterogeneous catalyst or unbound to the heterogeneous catalyst and added separately to the condensation reaction. Non-limiting examples of bound promoters include mercaptoalkylpyridines, mercaptoalkylamines, thiazolidines and aminothiols. Non-limiting examples of unbound promoters include alkyl mercaptans, such as methyl mercaptan (MeSH) and ethyl mercaptan, mercaptocarboxylic acids, such as mercaptopropionic acid, and mercaptosulfonic acids.

The amount of organic sulfur-containing promoter employed in the catalyst system depends on the particular acidic heterogeneous catalyst employed and the condensation process to be catalyzed. In general, however, the organic sulfur-containing promoter is employed in an amount from 2 to 30 mol %, such as 5 to 20 mol %, based on the sulfonic groups in the acid catalyst.

Use of the Catalyst System in Condensation Reactions

The catalysts system described above is found to have activity in condensation reactions, particularly condensation reactions between a carbonyl compound reactant and a phenolic compound reactant to produce a polyphenol product. Examples of suitable carbonyl compounds are those compounds represented by the following formula:

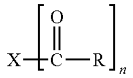

wherein R represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated; n is greater than 0, preferably from 1 to 3, more preferably from 1-2, and most preferably is 1; and when n is greater than 1, X represents a bond, or a multivalent linking group having from 1 to 14 carbon atoms, preferably from 1 to 6 carbon atoms, more preferably from 1 to 4 carbon atoms; and when n is 1, X represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated, provided that X and R are not both hydrogen.

Suitable carbonyl compounds for use herein include aldehydes and ketones. These compounds generally contain from three to fourteen carbon atoms, and are preferably aliphatic ketones. Examples of suitable carbonyl compounds include ketones such as acetone, methyl ethyl ketone, diethyl ketone, dibutyl ketone, isobutyl methyl ketone, acetophenone, methyl and amyl ketone, cyclohexanone, 3,3,5-trimethylcyclohexanone, cyclopentanone, 1,3-dichloroacetone and the like. The most preferred is acetone.

The carbonyl compounds are reacted with phenolic compounds. Phenolic compounds are aromatic compounds containing an aromatic nucleus to which is directly bonded at least one hydroxyl group. Phenolic compounds suitable for use herein include phenol and the homologues and substitution products of phenol containing at least one replaceable hydrogen atom directly bonded to the aromatic phenol nucleus. Such groups substituting for the hydrogen atom and directly bonded to the aromatic nucleus include the halogen radicals such as chloride and bromide, and the hydrocarbon radicals such as alkyl, cycloalkyl, aryl, alkaryl and aralkyl groups. Suitable phenolic compounds include phenol, the cresols, the xylenols, carvacrol, cumenol, 2-methyl-6-ethyl phenol, 2,4-dimethyl-3-ethylphenol, o-chlorophenol, m-chlorophenol, o-t-butylphenol, 2,5-xylenol, 2,5-di-t-butylphenol, o-phenylphenol, 4-ethylphenol, 2-ethyl-4-methylphenol, 2,3,6-trimethylphenol, 2-methyl-4-tert-butylphenol, 2-tertbutyl-4methylphenol, 2,3,5,6-tetramethylphenols, 2,6-dimethylphenol, 2,6-ditertbutylphenol, 3,5-dimethylphenol, 2-methyl-3,5-diethylphenol, o-phenylphenol, p-phenylphenol, naphthols, phenanthrol, and the like. Most preferred are compositions comprising phenol. Mixtures of any of the above may be used.

The above is not meant to limit the invention but to illustrate representative examples of carbonyl compounds and phenolic compounds which are known in the art to make desirable polyphenol and for which those of skill in the art can substitute other similar reactants.

In the preparation of the polyphenols, an excess of the phenolic compound reactant over the carbonyl compound reactant is usually desirable. Generally, at least about 2, preferably from about 4 to about 25, moles of phenolic compound per mole of carbonyl compound is desirable for high conversion of the carbonyl compound. Solvents or diluents are not necessary in the process of the present invention for the manufacture of the polyphenol except at low temperature.

The polyphenol compounds obtained by the condensation reaction of a phenolic compound and a carbonyl compound in the present process are compounds wherein the nuclei of at least two phenolic radicals are directly attached by carbon to carbon linkages to the same single carbon atom in the alkyl group. An illustrative non-limiting example of a polyphenol compound is represented by the formula:

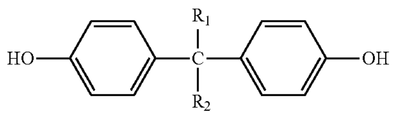

wherein $R^1$ and $R^2$ each independently represent a monovalent organic radical. Examples of such radicals include hydrocarbon radicals such as aliphatic, cycloaliphatic, aromatic, or heterocyclic, more specifically hydrocarbon radicals, such as alkyl, cycloalkyl, aryl, aralkyl, or alkaryl, whether saturated or unsaturated. Preferably, $R^1$ and $R^2$ each independently represent an alkyl radical having from 1 to 2 carbon atoms. Most preferably, the polyphenol compound comprises 2,2-bis (4-hydroxyphenyl) propane, i.e. bisphenol-A (BPA).

The reaction conditions used to effect the condensation reaction described above will vary depending on the type of phenolic compound, solvent, carbonyl compound, and condensation catalyst selected. Generally, the phenolic compounds and the carbonyl compounds are reacted in a reaction vessel, whether in the batch or continuous mode, at a temperature ranging from about 20° C. to about 130° C., preferably from about 50° C. to about 90° C.

The pressure conditions are not particularly limited and the reaction may proceed at atmospheric, sub atmospheric or super atmospheric pressure. However, it is preferred to run the reaction either without any externally induced pressure, or at sufficient pressure to force the reaction mixture across a catalyst bed or to force the reaction mixture upstream in a vertical reactor, or to maintain the contents of the reaction vessel in a liquid state if the reaction is run at a temperature above the boiling point of any ingredient. The pressure and temperature should be set under conditions to retain the reactants in the liquid phase in the reaction zone. The temperature may exceed 130° C., but should not be so high as to degrade any of the ingredients in the reaction vessel, nor should it be so high as to degrade the reaction product or promote the synthesis of a substantial amount of unwanted by-products.

The reactants are introduced into the reaction zone under conditions to assure a molar excess of the phenolic compound over the carbonyl compound. Preferably, the phenolic compound is reacted in a substantial molar excess over the carbonyl compound. For example, the molar ratio of the phenolic compound to the carbonyl compound is preferably at least about 2:1, more preferably at least about 4:1, and up to about 25:1.

Where the unbound thiol promoter is methyl mercaptan, and the carbonyl compound is acetone, 2,2-bis(methylthio) propane (BMTP) is formed in the presence of an acidic catalyst. In the presence of a hydrolyzing agent, BMTP dissociates in the reaction zone into methyl mercaptan and acetone as acetone is condensed with phenol to form BPA. A convenient hydrolyzing agent is water, which may be introduced into any of the feed charges, directly into the reaction zone, or may be produced in situ by the condensation reaction between the carbonyl compound and the phenolic compound. A molar ratio of water to BMTP catalyst promoter ranging from about 1:1 to about 5:1 is sufficient to adequately hydrolyze the BMTP catalyst promoter. This quantity of water is produced in situ under typical reaction conditions. Thus, additional water does not need to be introduced into the reaction zone, although water may optionally be added if desired.

Any suitable reactor may be used as the reaction zone. The reaction can occur in a single reactor, or in a plurality of reactors connected in series or in parallel. The reactor can be a back mixed or plug flow reactor, and the reaction can be conducted in a continuous or batch mode, and the reactor can be oriented to produce an up-flow or down-flow stream. In the case of the fixed bed flow system, the liquid space velocity of the mixture of the raw materials supplied to the reactor is usually 0.2 to 50 $hr^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

Any method known to those of skill in the art may be employed to recover the polyphenol compound. Generally, however, the crude reaction mixture effluent from the reaction zone is fed to a separator, such as a distillation column. The polyphenol product, polyphenol isomers, unreacted phenolic compound, and a small amount of various impurities are removed from the separator as a bottoms product. This bottoms product may be fed to a further separator. While crystallization is a common method of polyphenol separation, any known method of separating polyphenol from the mother liquor can be used depending upon the desired degree of purity of the polyphenol product. Once separated, the mother liquor comprising phenol and polyphenol isomers may be returned to the reaction zone as reactants.

The invention will now be more particularly described with reference to the following non-limiting Examples and the accompanying drawings.

Example 1

Separate samples of a mixture of 8% by weight BPA, 85.5% by weight phenol, 5% by weight acetone, 1% by weight sulfur promoter and 0.5% by weight water were contacted at 75° C. with the following catalysts:

(a) a commercially available ion exchange resin (IER), Purolite® CT-122 MR8-711;

(b) propanesulfonic acid silica (pKa=3.3) [also referred to herein as alkylsulfonic acid silica]; and (c) ethylbenzenesulfonic acid silica (pKa=3.4) [also referred to herein as arylsulfonic acid silica].

Both the propanesulfonic acid silica and the ethylbenzenesulfonic acid silica were as supplied by Silicycle.

In each test, amount of catalyst employed was equivalent to an acid capacity of 5.17 meq.

The sulfur promoter was added as 2,2-bis(methylthio) propane which was added in an amount sufficient to reach 1% by weight of methanethiol ($CH_3SH$) in the reaction mixture.

The selectivity of the catalysts to the production of BPA as a function of acetone conversion are shown in FIG. 1, from which it will be seen that the Purolite® CT-122 exhibited a p,p-BPA selectivity of about 92.4% over the range of acetone conversion levels tested (50% to 100% conversion), while both the organosulfonic acid silicas exhibited a p,p-BPA selectivity in excess of 94% over a similar range of acetone conversion levels.

The relative reaction rate and selectivity of the functionalized catalysts (alkyl and aryl sulfonic acid silica) and the ion exchange resin after 0.75 hour are shown in Table 1.

TABLE 1

| | Relative reaction rate | p,p-BPA Selectivity (%) |
|---|---|---|
| IER (Purolite ®) | 0.6 | 92.9 |
| Alkylsulfonic acid silica | 0.8 | 94.9 |
| Arylsulfonic acid silica | 1 | 94.6 |

It will be seen from Table 1 that the acetone reaction rate decreases in the order: aryl sulfonic acid>alkyl sulfonic acid>IER. Considering that the reactors were loaded with the same acid site number, the arylsulfonic acid silica was found to be 1.7 times more active than the ion exchange resin. It will also be seen from Table 1 and FIG. 1 that the selectivity depended on the functional group type, to which the alkylsulfonic acid silica shows a higher selectivity toward p,p-BPA formation than the arylsulfonic acid silica. A high p,p-BPA selectivity is desirable since the capital and operating costs of the downstream purification processes can be reduced.

Example 2

Figure 2:
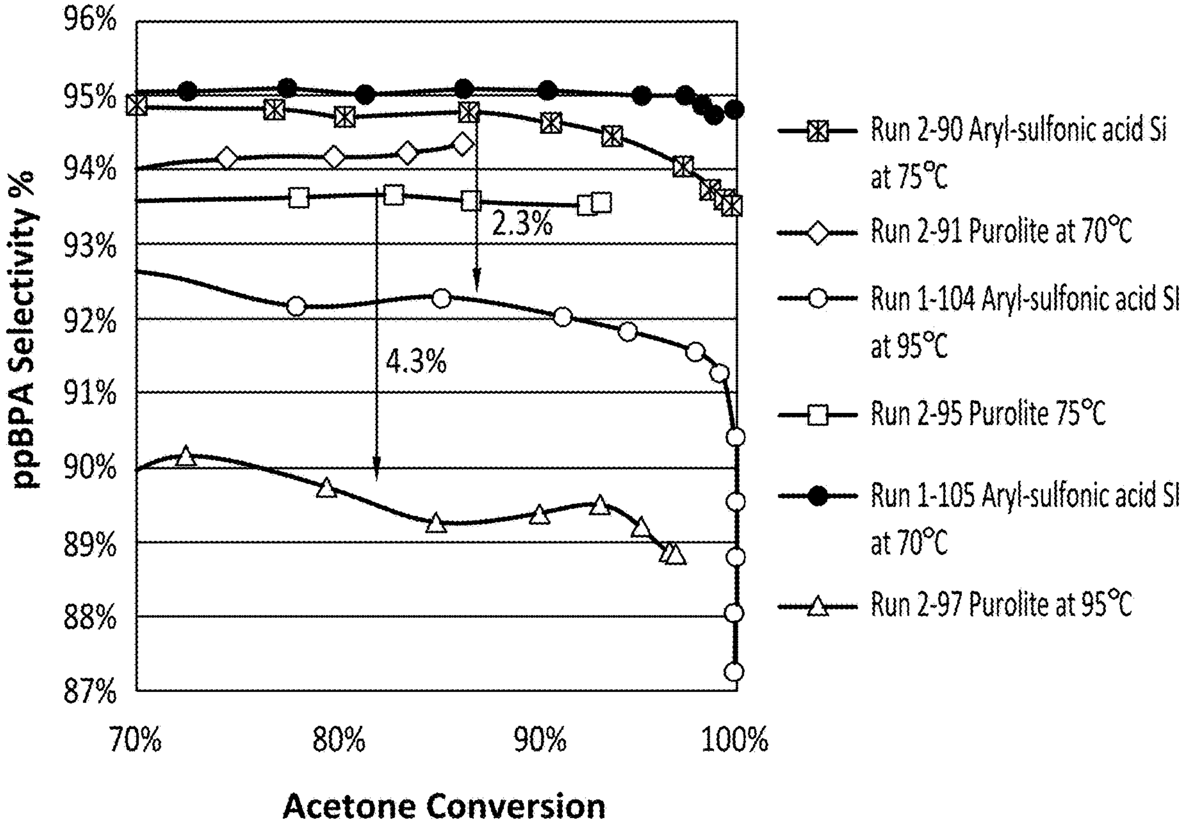
FIG. 2 is a graph of BPA selectivity against temperature for Purolite® CT-122 and an arylsulfonic acid silica in the condensation of phenol and acetone according to the process of Example 2.

The process of Example 1 was repeated with the ion exchange resin and the arylsulfonic acid silica catalysts and with the temperature being varied over a range from 70-95° C. The results are shown in FIG. 2. As expected, the activity increases as temperature increases while the selectivity decreases. As shown in FIG. 2, a 4.3% selectivity drop was found with the ion exchange resin when reaction temperature increases 20° C., while sulfonic acid silica exhibits only a 2.3% selectivity drop for the same temperature increase. It indicates that the sulfonic acid silicas are less sensitive to reaction temperature changes than the conventional resin catalysts.

Example 3

Figure 3A:
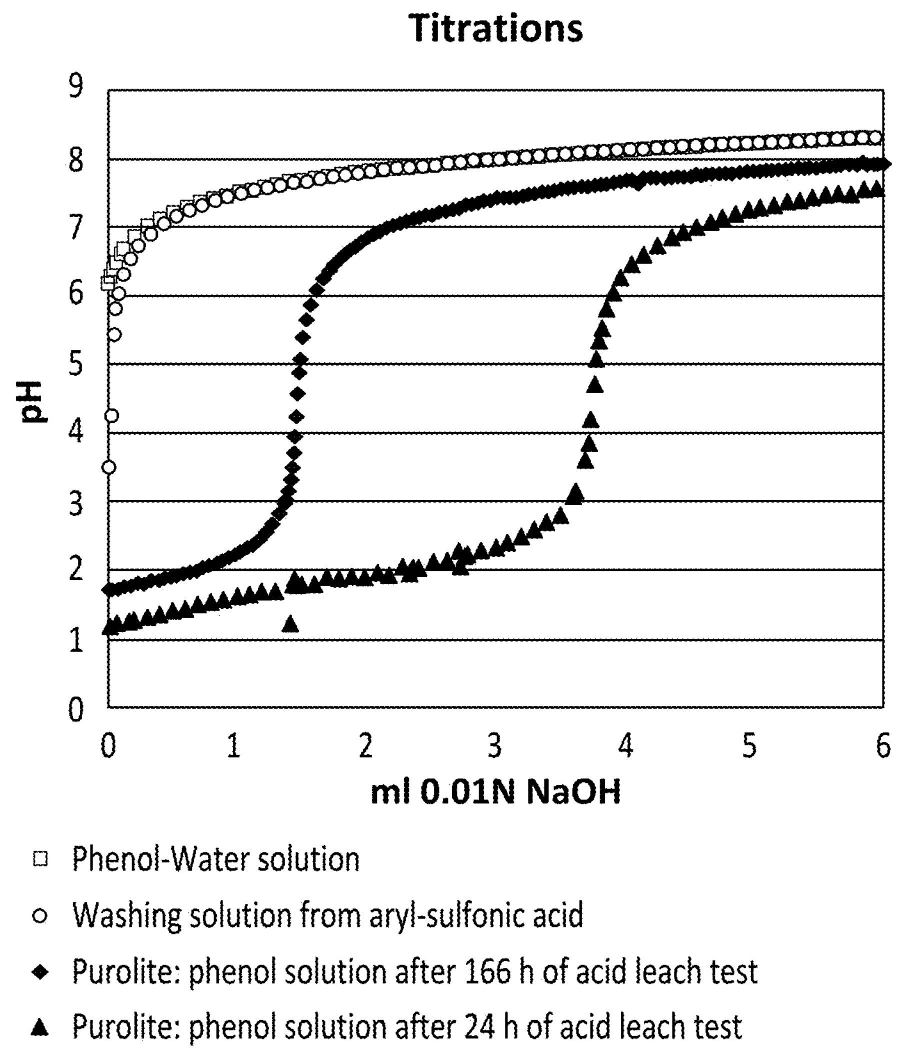
FIGS. 3(*a*) and 3(*b*) show the results of the acid leaching test of Example 3 on the ion exchange resin Purolite® CT-122 and the arylsulfonic acid silica.
Figure 3B:
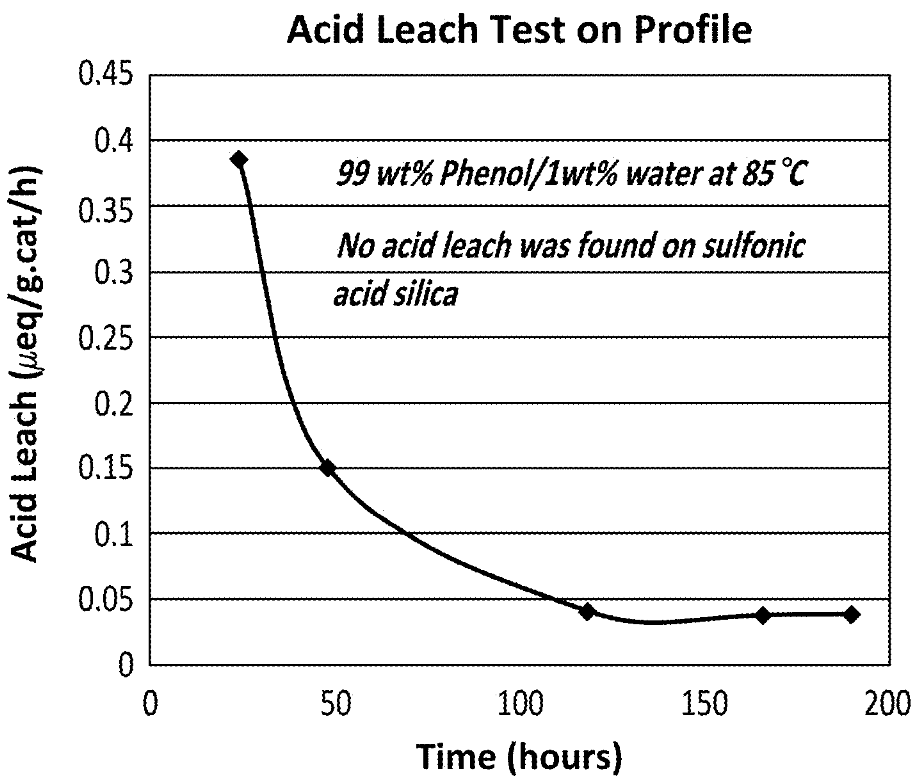

In this Example, the resistance to acid leaching of the ion exchange resin (Purolite® CT-122) catalyst and the arylsulfonic acid silica (ethylbenzenesulfonic acid silica) catalyst were compared. The acid leaching test involved mixing the dry catalyst with 1 wt % water/99 wt % phenol, and holding at 85° C. The supernatant liquid was removed and titrated with 0.01 N NaOH at specific times. The results are shown in FIGS. 3(*a*) and (*b*) and reveal a high acid leach rate for the ion exchange resin which reaches a constant rate after several lixiviation procedures. On the other hand, the water-phenol mixture possesses a similar titration curve to that of arylsulfonic acid silica catalyst. This led to the conclusion that there is no acid leaching with the sulfonic acid silica catalyst.

Example 4

Figure 4:
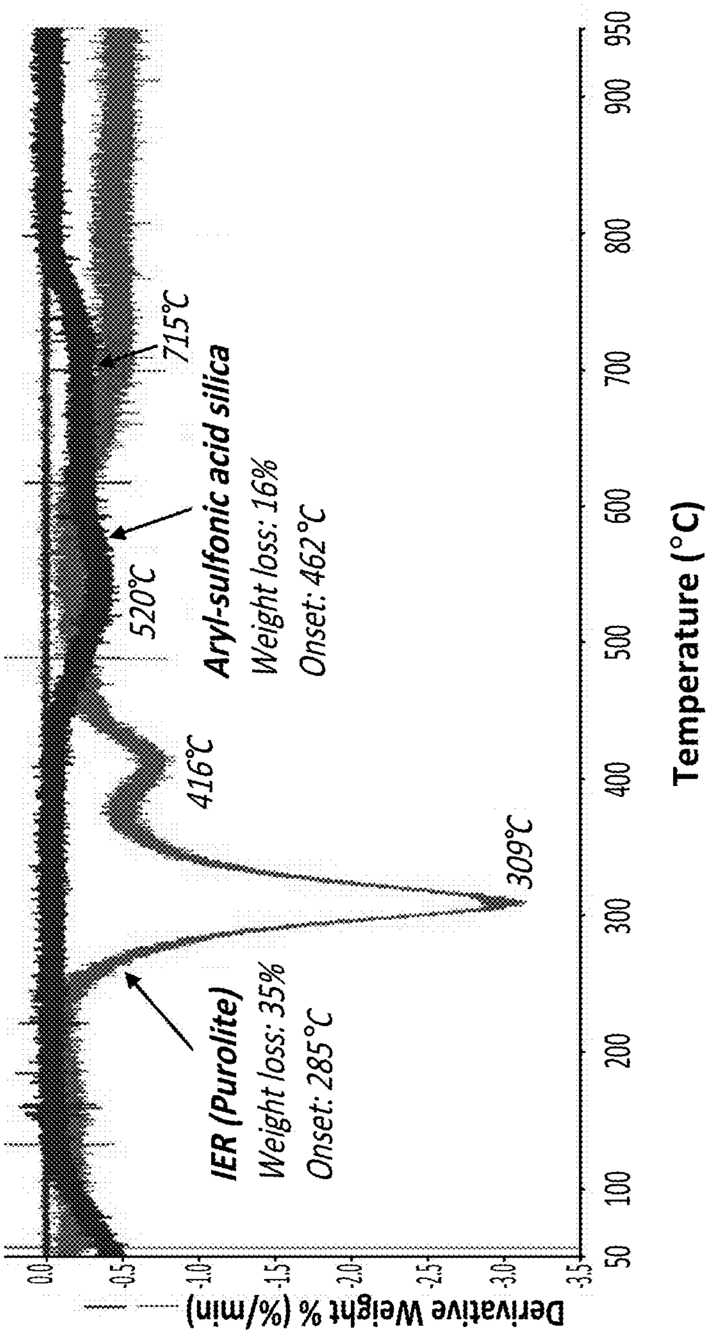
FIG. 4 compares the results of the thermogravimetric analysis (TGA) test of Example 4 on the ion exchange resin Purolite® CT-122 and the arylsulfonic acid silica.

In this Example, thermogravimetric analysis was used to determine the thermal stability of the arylsulfonic acid silica functionalized catalyst in comparison with the ion exchange resin. In the test, each catalyst was initially heated at 60° C. under vacuum to eliminate adsorbed water and was then heated to 950° C. at a ramp rate of 5° C./min while 20 mL/min of nitrogen was passed over the catalyst. The TGA thermograms are shown in FIG. 4. The sulfonic acid groups were decomposed in two stages: one at low temperature and the second at higher temperature which likely depends on the sulfonic species type and its interaction with the support. The sulfonic groups decomposition starts at 285° C. in IER and at 462° C. in arylsulfonic acid silica. The higher decomposition onset temperature is a clear indication that the sulfonic acid silica is more stable than the ion exchange resin.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A catalyst system useful in the production of bisphenol-A comprising:

(a) an acidic heterogeneous catalyst comprising amorphous silica having organosulfonic acid groups chemically bonded thereto, wherein the catalyst has a pKa value of 3.5 or less; and (b) a catalyst promoter comprising at least one organic sulfur-containing compound, wherein the at least one organic sulfur-containing compound is employed in an amount from 5 to 20 mol %, based on the organosulfonic acid groups in the acidic heterogeneous catalyst.

2. The catalyst system of claim 1, wherein the amorphous silica comprises separate silica particles.

3. The catalyst system of claim 1, wherein the amorphous silica comprises extrudates comprising silica particles.

4. The catalyst system of claim 1, wherein the amorphous silica is substantially free of zirconium.

5. The catalyst system of claim 1, wherein the acidic heterogeneous catalyst comprises amorphous silica having bonded thereto organosulfonic acid groups having the following formula —$R^1SO_3H$ where $R^1$ is a substituted or unsubstituted alkyl, alkenyl, or alkynyl group having up to 8 carbon atoms or is a substituted or unsubstituted aryl group.

6. The catalyst system of claim 5, wherein $R^1$ is an alkyl group having from 1 to 4 carbon atoms.

7. The catalyst system of claim 5, wherein $R^1$ is an alkyl-substituted phenyl group in which the alkyl moiety has from 1 to 4 carbon atoms.

8. The catalyst system of claim 1, wherein the at least one organic sulfur-containing compound is selected from the group consisting of alkyl mercaptans, mercaptocarboxylic acids, mercaptosulfonic acids, mercaptoalkylpyridines, mercaptoalkylamines, thiazolidines and aminothiols.

9. The catalyst system of claim 1, wherein the catalyst promoter is chemically bonded to the amorphous silica.

10. The catalyst system of claim 1, wherein the catalyst promoter is chemically and physically separate from the amorphous silica.

* * * * *